United States Patent [19]

Trager et al.

[11] Patent Number: 4,540,568

[45] Date of Patent: Sep. 10, 1985

[54] INJECTIONABLE VISCOELASTIC OPHTHALMIC GEL

[76] Inventors: Seymour F. Trager, 14 Sherwood Dr., Plainview, N.Y. 11803; Victoria S. Chylinski, 11 Peghouse Rise, Slad Rd., Stroud, Glos., England

[21] Appl. No.: 625,249

[22] Filed: Jun. 27, 1984

Related U.S. Application Data

[63] Continuation-in-part of Ser. No. 434,412, Oct. 14, 1982, abandoned.

[51] Int. Cl.³ .............................................. A61K 31/78
[52] U.S. Cl. ....................................... 424/81; 514/912
[58] Field of Search ................................... 424/78, 81

[56] References Cited

U.S. PATENT DOCUMENTS

| | | | |
|---|---|---|---|
| 3,868,445 | 2/1975 | Ryde et al. | 424/14 |
| 3,920,810 | 11/1975 | Rankin | 424/80 |
| 3,978,201 | 8/1976 | Khromov et al. | 424/81 |
| 4,003,991 | 1/1977 | Krohn et al. | 424/81 |

OTHER PUBLICATIONS

Chem. Abst., 76, 90018(h) (1972), Leong et al.
Chem. Abst., 76, 90019(j) (1972), Lemp et al.

*Primary Examiner*—Douglas W. Robinson
*Attorney, Agent, or Firm*—Fidelman, Wolffe and Waldron

[57] ABSTRACT

An improved injectionable viscoelastic gel for use in opthalmic surgical and treatment procedures, wherein the gelling agent is a high molecular weight polyacrylamide or polymethacrylamide.

6 Claims, No Drawings

INJECTIONABLE VISCOELASTIC OPHTHALMIC GEL

BACKGROUND OF THE INVENTION

This invention relates to ophthalmic surgery and treatment. More particularly, this invention relates to a composition particularly suitable for use as an adjunct in ophthalmic surgery.

In surgical procedures involving ocular tissue such as, for example, anterior segment surgery, it is always necessary to protect the corneal endothelium from mechanical damage. Failure to provide adequate protection can result in irreparable damage to the tissue.

Presently, ophthalmic surgical procedures are carried out in a viscoelastic medium so as to prevent mechanical damage and denudation of the tissue surfaces. Sodium hyaluronate is currently widely used as the viscoelastic substance, presenting both positive and negative facets in ophthalmic surgical procedures. Positively, the hyaluronate has been reported as protecting the corneal endothelium; however, great care must be exercised in the use of hyaluronate, and in many instances, undesirable post-operative pressure increases have been noted, with dilation and, in some instances, adhesion development between the posterior capsule and the iris.

It is an object of the present invention to provide an improved injectionable ocular surgical and treatment adjunct.

It is a further object of the present invention to provide an improved injectionable viscoelastic solution which is nonreactive with ocular tissues.

A further object of the present invention is to provide an improved injectionable viscoelastic solution which may be employed without postoperative complications in such anterior segment surgical procedures as cataract removal, corneal transplants, penetrating keratoplasty, correctional treatment of bullous rhegmatogenous retinal detachment and the like.

These and other objects will become apparent from the disclosure which follows.

STATEMENT OF THE INVENTION

In accordance with the present invention, there is provided an improved viscoelastic gel comprising:
an acrylamide polymer selected from polyacrylamide and polymethacrylamide
sodium chloride
potassium chloride
calcium chloride
magnesium chloride hexahydrate
sodium acetate
buffer
water In this particularly effective formulation, it has been found that the effectiveness thereof is achieved by compounding the constituents thereof within certain, well-defined ranges and by employing polyacrylamides and polymethacrylamides of certain, well-defined molecular weights.

The polyacrylamides found to be effective in the present compositions are polymers having a molecular weight of from about 1 to about 6 million, produced by the polymerization of acrylamide, methacrylamide, or mixtures thereof by methods known to the art. Preferably, the polymers have a molecular weight on the order of about 5 million. Inclusion of the polymer in the gel formulation is maintained within from about 2 to about 5 percent by weights, preferably from about 3.5 to about 4.5 percent by weight, and most preferably about 4.0 percent by weight.

The remaining constituents of the formulation are present in the following amounts, based upon percent by weight:

| | |
|---|---|
| sodium chloride | 0.4–8.6 |
| potassium chloride | 0.075–0.3 |
| calcium chloride | 0.04–0.33 |
| magnesium chloride hexahydrate | 0.02–0.04 |
| sodium acetate | 0.3–0.4 |
| buffer | 0.15–0.20 |
| water | remainder |

A particularly suitable formulation is a 4.0 percent by weight polymer gel containing 0.49 percent by weight sodium chloride, 0.075 percent by weight potassium chloride, 0.048 percent by weight calcium chloride, 0.03 magnesium chloride hexahydrate and 0.17 sodium citrate dihydrate as the buffering agent.

While sodium citrate dihydrate is preferred as a gel buffer, other pharmaceutically acceptable buffering agents such as sodium phosphates and sodium borates may be advantageously employed.

The composition is formulated by autoclaving at sterilization temperatures an 8-10 percent by weight of the polymer and admixing the sterile gel with the premixed salt solution. It has been found that compounding of the polymer with the salt constituents prior to sterilization results in a rise in pH above an acceptable level.

The viscoelastic gels of the present invention are, as previously stated, particularly useful in ocular surgical procedures as a surgical adjunct, exhibiting:

(a) protective properties for corneal endothelium, iris and retinal tissue;

(b) superior properties as an aqueous humor replacement;

(c) ability to maintain a deep anterior chamber during operative procedures;

(d) ability to separate effectively tissue surfaces and thereby minimize adhesion; and (e) biocompatibility with intra ocular tissues.

The particular effectiveness of this specific formulation as an adjunct in ophthalmic surgery is a direct result of its balanced viscoelastic properties. The viscous nature thereof provides mechanical protection for tissues (iris, retina) and cell layers (corneal endo- and epithelium) which may be exposed to mechanical damage during surgery. Further, due to the physical properties of the formulation, the gel does not flow out of the anterior chamber, providing a deep anterior chamber during surgical manipulations.

The following example serves to illustrate the present invention.

EXAMPLE 1

An autoclaved polyacrylamide having a molecular weight of about 5 million was admixed with a premixed salt solution to yield the following homogenous gel composition:

| Component | Percent by Weight |
|---|---|
| polyacrylamide | 4.0 |
| sodium chloride | 0.049 |
| potassium chloride | 0.075 |

| Component | Percent by Weight |
|---|---|
| calcium chloride | 0.048 |
| magnesium chloride hexahydrate | 0.030 |
| sodium acetate | 0.390 |
| sodium citrate dihydrate | 0.170 |
| water | remainder |

The gel, when utilized in standard testing for biocompatibility and irritation determinations, produced no adverse reactions in the ocular tissues of the test animals.

EXAMPLE 2

An autoclaved polymethacrylate having a molecular weight of about 5 million was admixed with a premixed salt solution to yield the following homogenous gel composition:

| Component | Percent by Weight |
|---|---|
| polymethacrylamide | 4.0 |
| sodium chloride | 0.049 |
| potassium chloride | 0.075 |
| calcium chloride | 0.048 |
| magnesium chloride hexahydrate | 0.030 |
| sodium acetate | 0.390 |
| sodium citrate dihydrate | 0.170 |
| water | remainder |

The gel, when utilized in standard testing for biocompatibility and irritation determinations, produced no adverse reactions in the ocular tissues of the test animals.

What is claimed is:

1. An injectionable viscoelastic gel particularly adapted for use in ophthalmic surgical procedures and treatments which gel consisting essentially of from about 2 to about 5 percent by weight of a polymer selected from polyacrylamide and polymethacrylamide, said polymer having a molecular weight of from about 1 to about 6 million; from about 0.4 to about 8.6 percent by weight sodium chloride, from about 0.075 to about 0.3 percent by weight postassium chloride, from about 0.04 to about 0.33 percent by weight calcium chloride, from about 0.02 to about 0.04 percent by weight magnesium chloride hexahydrate, from about 0.3 to about 0.4 percent by weight sodium acetate, from about 0.15 to about 0.20 percent by weight of a buffer, remainder water.

2. A gel as defined in claim 1 wherein said polymer is polyacrylamide.

3. A gel as defined in claim 1 wherein said polymer is present in an amount of from about 3.5 to about 4.5 percent by weight.

4. A gel as defined in claim 1 wherein said polymer has a molecular weight of from about 4.5 to about 5.5 million.

5. A gel as defined in claim 1 wherein said buffer is sodium citrate dihydrate.

6. A gel as defined in claim 1 consisting essentially of about 4 percent by weight of said polymer having a molecular weight of about 5 million, about 0.49 percent by weight sodium chloride, about 0.075 percent by weight potassium chloride, about 0.048 percent by weight calcium chloride, about 0.03 percent by weight magnesium chloride hexahydrate, about 0.17 percent by weight sodium citrate dihydrate, remainder water.

* * * * *